United States Patent
Sato et al.

(10) Patent No.: US 6,835,788 B2
(45) Date of Patent: Dec. 28, 2004

(54) CATALYST FOR VINYL COMPOUND POLYMERIZATION AND PROCESS FOR PRODUCING VINYL POLYMER

(75) Inventors: Haruhito Sato, Chiba (JP); Masami Watanabe, Chiba (JP); Masahiko Kuramoto, Chiba (JP)

(73) Assignee: Idemitsu Petrochemical Co., Ltd., Tokyo (JP)

( * ) Notice: Subject to any disclaimer, the term of this patent is extended or adjusted under 35 U.S.C. 154(b) by 12 days.

(21) Appl. No.: 10/204,262

(22) PCT Filed: Mar. 5, 2001

(86) PCT No.: PCT/JP01/01690
§ 371 (c)(1),
(2), (4) Date: Aug. 20, 2002

(87) PCT Pub. No.: WO01/66603
PCT Pub. Date: Sep. 13, 2001

(65) Prior Publication Data
US 2003/0027716 A1 Feb. 6, 2003

(30) Foreign Application Priority Data
Mar. 6, 2000 (JP) ........................ 2000-059866

(51) Int. Cl.$^7$ ................................ C08F 4/42
(52) U.S. Cl. .................... 526/161; 526/160; 526/943; 526/155; 526/171; 502/80; 502/152; 502/104; 502/108; 502/132
(58) Field of Search ................... 526/160, 161, 526/943, 155, 171; 502/80, 152, 104, 108, 132

(56) References Cited

U.S. PATENT DOCUMENTS

| 6,335,405 B1 * | 1/2002 | Okuda et al. ........... 526/161 |
| 6,555,633 B1 * | 4/2003 | Tanaka et al. ........... 526/160 |

FOREIGN PATENT DOCUMENTS

| EP | 511665 | 11/1992 |
| EP | 0 511 665 A2 * | 11/1992 |
| EP | 945471 | 9/1999 |
| EP | 0 945 471 A1 * | 9/1999 |
| JP | 5-25214 | 2/1993 |
| JP | 7-149671 | 6/1995 |
| JP | 10-204114 | 8/1998 |
| WO | 99/48930 | 9/1999 |
| WO | 00/43123 | 7/2000 |
| WO | 00/76659 | 12/2000 |

* cited by examiner

Primary Examiner—Ling Siu Choi
(74) Attorney, Agent, or Firm—Oblon, Spivak, McClelland, Maier & Neustadt, P.C.

(57) ABSTRACT

The catalyst for polymerizing vinyl compounds according to the present invention comprises (A) a complex of Group 4 to 10 transition metal of the Periodic Table, (B) a clay, clay mineral or ion-exchangeable layered compound, and (C) at least one aluminoxy compound represented by Formula (1):

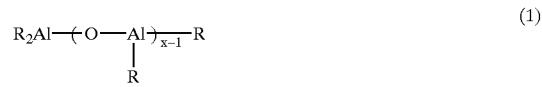

wherein a plurality of R groups are each independently $C_{1-10}$ hydrocarbon group and at least one of the R groups is a hydrocarbon group having 2 or more carbon atoms; and x is an integer of 2 or more. By using the Group 4 to 10 transition metal complex and the clay, clay mineral or ion-exchangeable layered compound in combination with the specific aluminoxy compound, vinyl polymers are produced at a high efficiency. Also, the catalyst for producing α-olefins according to the present invention comprises (A') a complex of Group 8 to 10 transition metal of the Periodic Table, (B') an organic compound-modified clay, clay mineral or ion-exchangeable layered compound, and (C') at least one aluminoxy compound represented by Formula (2):

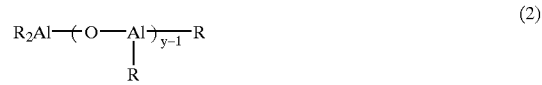

wherein a plurality of R groups are each independently $C_{1-10}$ hydrocarbon group and at least one of the R groups is a hydrocarbon group having 2 or more carbon atoms; and y is an integer of 2 to 4. Since the organic compound-modified clay, clay mineral or ion-exchangeable layered compound absorbs other catalyst components between layers thereof, the elution of the catalyst components into liquid phase is effectively prevented, thereby facilitating the separation of the catalyst from a reaction product.

34 Claims, No Drawings

CATALYST FOR VINYL COMPOUND POLYMERIZATION AND PROCESS FOR PRODUCING VINYL POLYMER

TECHNICAL FIELD

The present invention relates to a catalyst for polymerizing vinyl compounds and a process for producing vinyl polymers using the catalyst, and more particularly, to a catalyst for polymerizing vinyl compounds which is capable of efficiently producing vinyl polymers having terminal vinyl bonds, and a process for producing vinyl polymers using such a catalyst.

BACKGROUND ART

Metallocene catalysts (Kaminsky catalysts) used together with methylaluminoxane (MAO) as a co-catalyst have been found to be useful as catalysts for the polymerization of olefins, and have been extensively studied. However, in order to allow the metallocene catalysts to exhibit its catalytic activity, it is necessary to use therewith a large amount of the expensive methyl aluminoxane. To solve the problem, for example, Japanese Patent Application Laid-Open No. 5-25214 has proposed to use a methylalumoxane co-catalyst supported on clay minerals (one of silicon-containing layered compounds) as a catalyst component for olefin-polymerizing catalyst, and specifically describes a methylalumoxane co-catalyst supported on smectite (clay minerals are used as a catalyst support). However, the preparation of such a co-catalyst inevitably requires to treat clays with a large amount of expensive and harmful methylalumoxane, and the obtained catalyst is still insufficient in polymerization activity per unit quantity of the aluminum component used. In addition, U.S. Pat. No. 5,308,811, etc., have proposed the use of clays treated with an aluminum compound such as trialkylaluminum as a co-catalyst, and specifically describes a catalyst composition comprising a metallocene complex, clay minerals, etc. However, the catalyst composition fails to achieve a sufficient polymerization activity for vinyl compounds only by treating clays with ordinary organoaluminum compounds. WO 99/02472 describes a process for producing α-olefins using a catalyst composed of a specific iron complex and an organoaluminum compound, and also describes the use of acidic clays such as montmorillonite as a support of activated catalysts or catalyst precursors. However, when methylaluminoxane described as a specific example of the organoaluminum compound is used as a catalyst component, the catalytic activity, especially the activity per unit quantity of aluminum, is still unsatisfactory.

Japanese Patent Application Laid-Open No. 8-295705 describes a process for producing α-olefins by the oligomerization of ethylene, in which α-olefins are separated from a reaction product to recover a catalyst and by-produced polymers. In this process, after separating α-olefins by distillation using an evaporator, the by-produced polymer and catalyst are recovered in the concentrated liquid residue. Also, Japanese Patent Application Laid-Open No. 10-45833 describes a process in which a reaction product solution is kept at a high temperature in order to inhibit the precipitation of by-produced polymer and facilitate subsequent treatments. In these conventional processes, since α-olefins are separated by distillation in the presence of the catalyst components, α-olefins are susceptible to side reactions such as isomerization. Further, Japanese Patent Application Laid-Open No. 7-149671 describes a process in which after preliminarily separating by-produced polymer, an ethylene oligomer (α-olefin) is separated and purified. In any of the prior art processes, ethylene is trimerized in the presence of a chromium catalyst to produce oligomers thereof. Further, these processes require an additional step for subjecting the catalyst components to deactivation or deashing treatment for removal thereof. In particular, in the process described in Japanese Patent Application Laid-Open No. 7-149671, since a homogeneous catalyst system comprising a chromium complex is used to enhance the catalytic activity, it is not possible to completely remove the catalyst components upon removal of the by-produced polymer. In addition, a pyrrole compound added to improve the activity of the chromium catalyst is difficult to remove, resulting in failure to purify α-olefins having 8 or more carbon atoms.

DISCLOSURE OF INVENTION

A first object of the present invention is to provide a catalyst for the polymerization of vinyl compounds which is capable of efficiently producing vinyl polymers having terminal vinyl bonds. A second object of the present invention is to provide a process for producing vinyl polymers using the above catalyst. A third object of the present invention is to provide a catalyst for the production of α-olefins which is readily separated from the reaction product after oligomerization reaction. A fourth object of the present invention is to provide a process for producing α-olefins using the above catalyst for the production of α-olefins in which the catalyst and by-produced polymer are readily separated from the reaction product.

As a result of the extensive studies for accomplishing the above objects, the inventors have found that vinyl polymers are efficiently produced in the presence of a catalyst comprising (A) a complex of Group 4 to 10 transition metal of the Periodic Table, (B) a clay, clay mineral or ion-exchangeable layered compound, and (C) a specific aluminoxy compound. The inventors have further found that α-olefins are efficiently produced in the presence of a catalyst comprising (A') a complex of Group 8 to 10 transition metal of the Periodic Table, (B') an organic compound-modified, clay, clay mineral or ion-exchangeable layered compound, and (C') a specific aluminoxy compound, and that the catalyst is readily separated from a reaction product. The present invention has been accomplished based on these findings.

Thus, the present invention provides a catalyst for polymerizing vinyl compounds comprising (A) a complex of Group 4 to 10 transition metal of the Periodic Table, (B) a clay, clay mineral or ion-exchangeable layered compound, and (C) at least one aluminoxy compound represented by the following general Formula (1):

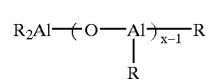

wherein a plurality of R groups are each independently a $C_{1-10}$ hydrocarbon group, and at least one of the R groups is a hydrocarbon group having 2 or more carbon atoms; and x is an integer of 2 or more.

The process for producing vinyl polymers comprises a step of polymerizing at least one vinyl compound selected from the group consisting of olefins, styrene, styrene derivatives, acrylic acid derivatives and vinyl esters of fatty acids in the presence of the catalyst for polymerizing vinyl compounds as defined above.

The present invention further provides a catalyst for producing α-olefins comprising (A') a complex of Group 8 to 10 transition metal of the Periodic Table, (B') an organic compound-modified, clay, clay mineral or ion-exchangeable layered compound, and (C') at least one aluminoxy compound represented by the following general Formula (2):

(2)

wherein a plurality of R groups are each independently a $C_{1-10}$ hydrocarbon group, and at least one of the R groups is a hydrocarbon group having 2 or more carbon atoms; and y is an integer of 2 to 4.

The process for producing α-olefins comprises a step of oligomerizing ethylene in the presence of the catalyst for producing α-olefins as defined above.

BEST MODE FOR CARRYING OUT THE INVENTION

The present invention will be described in detail below.

[I] Catalyst for Polymerization of Vinyl Compounds

The catalyst for polymerizing vinyl compounds according to the present invention comprises (A) a complex of Group 4 to 10 transition metal of the Periodic Table, (B) a clay, clay mineral or ion-exchangeable layered compound, and (C) at least one aluminoxy compound represented by the following general Formula (1):

(1)

wherein a plurality of R groups are each independently a $C_{1-10}$ hydrocarbon group, and at least one of the R groups is a hydrocarbon group having 2 or more carbon atoms; and x is an integer of 2 or more.

The respective components of the catalyst for polymerizing vinyl compound are explained below.

Component (A)

The component (A), generally called a main catalyst, is a complex of Groups 4 to 10 transition metal of the Periodic Table. Examples of the transition metal complexes include metallocene complexes of Group 4 to 6 transition metals and chelate complexes of Group 4 to 10 transition metals.

As the metallocene complexes, there may be used those known in the arts. Examples of the metallocene complexes include transition metal complexes containing one or two ligands selected from cyclopentadienyl, substituted cyclopentadienyl, indenyl and substituted indenyl, as well as transition metal complexes having its ligand geometrically confined, as described in Japanese Patent Application Laid-Open Nos. 58-19309, 61-130314, 3-163088, 4-300887, 4-211694 and 1-502036. The transition metal of the transition metal complexes is preferably zirconium, titanium or hafnium.

Specific examples of the metallocene complexes include cyclopentadienyl zirconium trichloride, pentamethylcyclopentadienyl zirconium trichloride, bis(cyclopentadienyl) zirconium dichloride, bis(pentamethylcyclopentadienyl) zirconium dichloride, bis(cyclopentadienyl) zirconium dialkyl, indenyl zirconium trichloride, bis(indenyl) zirconium dichloride, dimethylsilylene-bis(indenyl) zirconium dichloride, (dimethylsilylene) (dimethylsilylene)-bis (indenyl) zirconium dichloride, (dimethylsilylene)-bis(2-methyl-4-phenylindenyl) zirconium dichloride, (dimethylsilylene)-bis(benzoindenyl) zirconium dichloride, ethylene-bis(indenyl) zirconium dichloride, (ethylene) (ethylene)-bis(indenyl) zirconium dichloride, (ethylene) (ethylene)-bis(3-methylindenyl) zirconium dichloride, (ethylene) (ethylene)-bis(4,7-dimethylindenyl) zirconium dichloride, 1,2-ethanediyl(t-butylamido)(tetramethyl-η5-cyclopentadienyl) zirconium dichloride, dimethylsilylene(t-butylamido)(tetramethyl-η5-cyclopentadienyl) zirconium dichloride,1,2-ethanediyl (methylamido)(tetramethyl-η5-cyclopentadienyl) zirconium dichloride, and those obtained by replacing the zirconium of the above complexes with titanium or hafnium.

Preferred complexes of Group 4 to 10 transition metal of the Periodic Table may include metal complexes represented by the following Formulas (3) and (4):

(3)

(4)

In the Formulas (3) and (4), $M^1$ is a Group 4 to 10 transition metal of the Periodic Table, preferably titanium, zirconium, hafnium, vanadium, chromium, iron, cobalt, nickel, palladium or platinum, and more preferably titanium, zirconium, iron, cobalt or nickel.

$L^1$ to $L^3$ are each independently a ligand capable of bonding to the transitional metal $M^1$ via a heteroatom. $L^1$ and $L^2$ of Formula (3) or $L^1$ to $L^3$ of Formula (4) are preferably bonded to each other to form a ring. Examples of the heteroatoms include nitrogen, oxygen and sulfur. Of these, nitrogen and oxygen are preferable. The nitrogen preferably forms an unsaturated bond with carbon, and more preferably forms —C=N— structural units called imine.

$X^1$ and $Y^1$ may be the same or different, and each represents a covalent- or ion-bonding ligand such as hydrogen; halogen; $C_{1-20}$ preferably $C_{1-10}$ hydrocarbon group; $C_{1-20}$ preferably $C_{1-10}$ alkoxy; amino; $C_{1-20}$ preferably $C_{1-12}$ phosphorus-containing hydrocarbon group such as diphenylphosphino; $C_{1-20}$, preferably $C_{1-12}$ silicon-containing hydrocarbon group; or halogen-containing boride anion such as $BF_4^-$. Preferred are halogen and $C_{1-20}$ hydrocarbon group. A plurality of $X^1$ groups and a plurality of $Y^1$ groups may be respectively the same or different from each other.

Each of m and n is independently 0 or a positive integer, and the sum of m and n is 0, 1, 2 or 3 depending on the valence of $M^1$.

Although not particularly limited, the transition metal complexes represented by Formula (3) are preferably chelate complexes having oxygen or nitrogen as the coordinating element. An example of the chelate complexes having nitrogen coordinated to metal is a diimine-containing complex compounds represented by the following Formula (5):

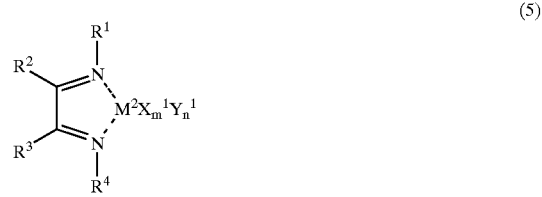

(5)

wherein $M^2$ is a Group 8 to 10 transition metal of the Periodic Table; $R^1$ and $R^4$ are each independently $C_{1-20}$ aliphatic hydrocarbon group, phenyl or $C_{7-20}$ aromatic group having a hydrocarbon group on its aromatic ring; $R^2$ and $R^3$ are each independently hydrogen or $C_{1-20}$ hydrocarbon group, and may be bonded together to from a ring; $X^1$ and $Y^1$ may be the same or different and are each a covalent- or ion-bonding group, and a plurality of $X^1$ groups and a plurality of $Y^1$ groups may be respectively the same or different; and m and n are each 0 or a positive integer, and the sum of m and n is 0, 1, 2 or 3 depending on the valence of $M^2$.

In the above Formula (5), $M^2$ is particularly preferably nickel and $X^1$ and $Y^1$ are each preferably halogen or $C_{1-20}$ hydrocarbon group, and more preferably chlorine or methyl. $C_{1-20}$ Aliphatic hydrocarbon group for $R^1$ and $R^4$ may include $C_{1-20}$ straight-chain or branched alkyl and $C_{3-20}$ cycloalkyl such as methyl, ethyl, n-propyl, isopropyl, n-butyl, isobutyl, s-butyl, t-butyl, pentyl, hexyl, octyl, decyl, tetradecyl, hexadecyl, octadecyl, cyclopentyl, cyclohexyl, and cyclooctyl. Cycloalkyl may have a suitable substituent such as lower alkyl on its ring. Examples of $C_{7-20}$ aromatic group which has a hydrocarbon group on the aromatic ring include those having one or more $C_{1-10}$ straight-chain, branched or cyclic alkyls on the aromatic ring such as phenyl and naphthyl. Preferred $R^1$ and $R^4$ are aromatic groups having a hydrocarbon group on the aromatic ring, and 2,6-diisopropylphenyl is particularly preferable. $R^1$ and $R^4$ may be the same or different from each other.

$C_{1-20}$ Hydrocarbon group for $R^2$ and $R^3$ may include $C_{1-20}$ straight-chain or branched alkyl, $C_{3-20}$ cycloalkyl, $C_{6-20}$ aryl, $C_{7-20}$ arylalkyl. Examples for $C_{1-20}$ straight-chain or branched alkyl and $C_{3-20}$ cycloalkyl are the same as those mentioned above. $C_{6-20}$ Aryl may be phenyl, tolyl, xylyl, naphthyl, methylnaphthyl, etc. $C_{7-20}$ Arylalkyl may be benzyl, phenethyl, etc. $R^2$ and $R^3$ may be the same or different from each other, and may be bonded to each other to form a ring.

Specific examples of the complex compounds represented by Formula (5) are shown below by Formulae [1] to [12].

[1]

[2]

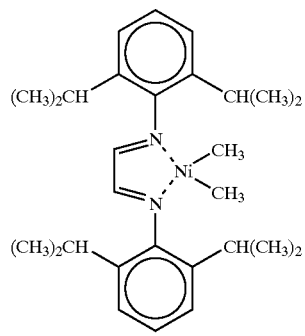

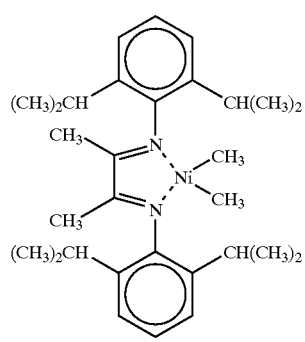

[3]

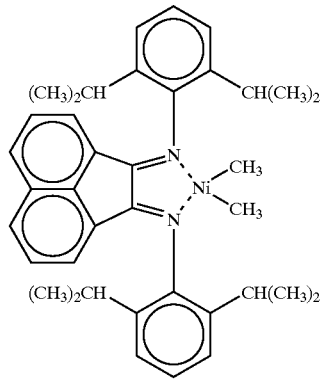

[4]

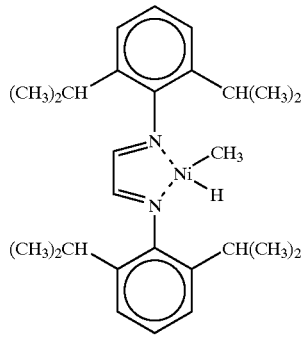

[5]

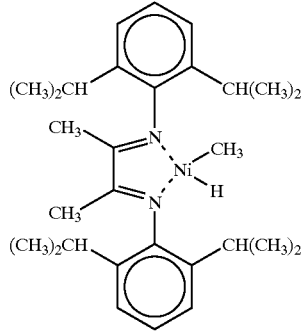

[6]

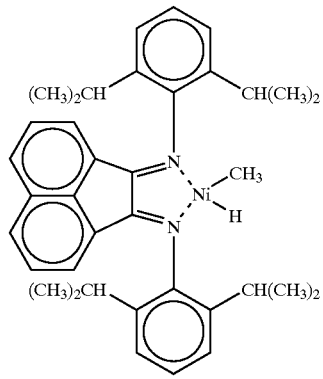

[7]
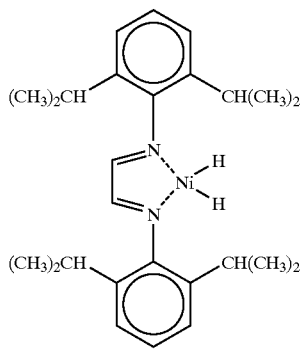

[8]
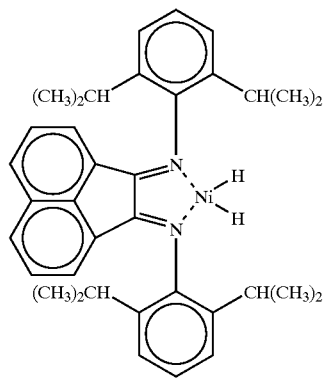

[9]
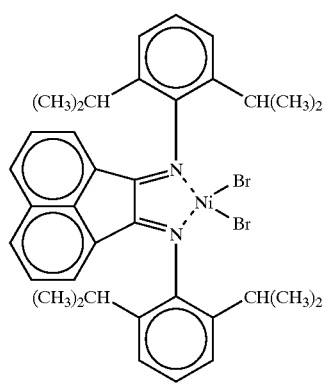

[10]

[11]
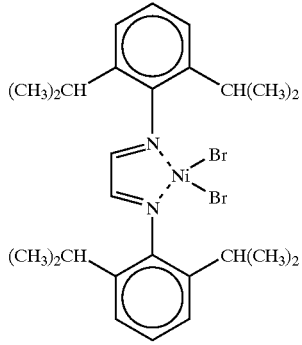

[12]
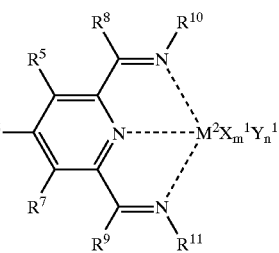

The transition metal complexes represented by Formula (4) are preferably nitrogen-containing iron, cobalt or nickel chelate complexes. Examples thereof are described in J. Am. Chem. Soc., 1998, 120, 4049–4050, Chem. Commun. 1998, 849–850, WO 98/27124, WO 99/02472 and WO 99/12981.

For example, the transition metal complex represented by Formula (4) may be a complex represented by the following Formula (6):

(6)

wherein $M^2$ is a Group 8 to 10 transition metal of the Periodic Table; $R^5$ to $R^9$ are each independently hydrogen, halogen, hydrocarbon group, substituted hydrocarbon group or heteroatom-containing hydrocarbon group, and may be bonded to each other to form a ring when each represents the hydrocarbon group; $R^{10}$ and $R^{11}$ are each independently $C_{1-160}$ aliphatic hydrocarbon group or $C_{7-160}$ aromatic group having a hydrocarbon group on the aromatic ring; $X^1$ and $Y^1$ may be the same or different and are each a covalent- or ion-bonding group, and a plurality of $X^1$ groups and a plurality of $Y^1$ groups may be respectively the same or different from each other; and m and n are each 0 or a positive integer and the sum of m and n is 0, 1, 2 or 3 depending on the valence of $M^2$.

In the above Formula (6), the hydrocarbon groups for $R^5$ to $R^9$ may include, for example, $C_{1-30}$ straight-chain or branched alkyl; $C_{3-30}$ cycloalkyl; $C_{6-30}$ aryl; $C_{7-30}$ arylalkyl;

etc. Specific examples of the $C_{1-30}$ straight-chain or branched alkyl include methyl, ethyl, n-propyl, isopropyl, n-butyl, isobutyl, s-butyl, t-butyl, different isomeric pentyl groups, different isomeric hexyl groups, different isomeric octyl groups, different isomeric decyl groups, different isomeric tetradecyl groups, different isomeric hexadecyl groups, different isomeric octadecyl groups, etc. Specific examples of the $C_{3-30}$ cycloalkyl include cyclopentyl, cyclohexyl, cyclooctyl, etc. The cycloalkyl may have a suitable substituent such as lower alkyl on its ring. Specific examples of the $C_{6-30}$ aryl include phenyl, tolyl, xylyl, naphthyl, methylnaphthyl, etc. Specific examples of the $C_{7-30}$ arylalkyl include benzyl, phenethyl, etc.

In the above Formula (6), the $C_{1-160}$ aliphatic hydrocarbon group for $R^{10}$ and $R^{11}$ may be the same as $C_{1-30}$ straight-chain or branched alkyl groups and $C_{3-30}$ cycloalkyl groups for $R^5$ to $R^9$. The $C_{7-160}$ aromatic groups having a hydrocarbon group on the aromatic rings may include, for example, phenyl and naphthyl having one or more $C_{1-10}$ straight-chain or branched alkyls or cyclic alkyls on their aromatic rings. $R^{10}$ and $R^{11}$ are preferably an aromatic group having a hydrocarbon group on its aromatic ring, and more preferably 2-methylphenyl and 2,4-dimethylphenyl.

$M^2$, $X^1$, $Y^1$, m and n in Formula (6) are the same as defined in the Formula (5). Preferred $M^2$ is iron, cobalt or nickel. $X^1$ and $Y^1$ are preferably halogen or $C_{1-20}$ hydrocarbon group, and more preferably chlorine or methyl.

Specific examples of the transition metal compound represented by Formula (6) may include iron or cobalt complexes having a ligand such as 2,6-diacetylpyridine bisimine compound, 2,6-diformylpyridine bisimine compound, 2,6-dibenzoylpyridine bisimine compound, etc. Particularly preferred are iron complexes having 2,6-diacetylpyridine bisimine compound as a ligand. Such complexes may be metal complexes represented by the following Formula (7):

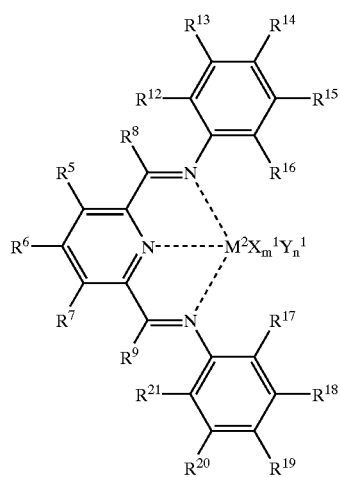

(7)

wherein $M^2$ is a Group 8 to 10 transition metal of the Periodic Table; $R^5$ to $R^9$ and $R^{12}$ to $R^{21}$ are each independently hydrogen, halogen, hydrocarbon group, substituted hydrocarbon group or heteroatom-containing hydrocarbon group, and any two adjacent groups of $R^{12}$ to $R^{21}$ may be bonded to each other to form a ring; $X^1$ and $Y^1$ may be the same or different and are each covalent- or ion-bonding group, and a plurality of $X^1$ groups and a plurality of $Y^1$ groups may be respectively the same or different from each other; and m and n are each 0 or a positive integer and the sum of m and n is 0, 1, 2 or 3 depending on the valence of $M^2$.

$R^5$ to $R^9$ and $R^{12}$ to $R^{21}$ of Formula (7) are each independently hydrogen, halogen, hydrocarbon group, substituted hydrocarbon group or heteroatom-containing hydrocarbon group. Examples of halogen include fluorine, chlorine, bromine and iodine. Examples of the hydrocarbon groups include $C_{1-30}$ hydrocarbon groups. Specific examples thereof include $C_{1-30}$ straight-chain hydrocarbon groups such as methyl, ethyl and n-propyl; $C_{3-30}$ branched hydrocarbon groups such as isopropyl, s-butyl and t-butyl; and $C_{3-30}$ alicyclic hydrocarbon groups such as cyclopentyl and cyclohexyl; and $C_{6-30}$ aromatic hydrocarbon groups such as phenyl and naphthyl. The substituted hydrocarbons are those obtained by substituting one or more hydrogen atoms of the above hydrocarbon groups with suitable substituents, e.g., $C_{1-30}$ substituted hydrocarbon groups. Examples of the substituents include hydrocarbon group, halogen, heteroatom-containing hydrocarbon group, etc. The hydrocarbon group as the substituent may be the same as defined above. Examples of the heteroatoms include nitrogen, oxygen, sulfur, etc. The substituted hydrocarbon groups may contain a heteroaromatic ring. The heteroatom-containing hydrocarbon group may be alkoxy represented by $—OR^{25}$, amino represented by $—NR^{25}{}_2$ or silyl represented by $—SiR^{25}{}_3$, wherein $R^{25}$ is the hydrocarbon group as mentioned above.

$R^{12}$ may be a primary, secondary or tertiary carbon group. When $R^{12}$ is a primary carbon group, zero to two of $R^{16}$, $R^{17}$ and $R^{21}$ may be a primary carbon group and the remainder thereof may be hydrogen. When $R^{12}$ is a secondary carbon group, zero or one of $R^{16}$, $R^{17}$ and $R^{21}$ may be a primary or secondary carbon group and the remainder may be hydrogen. When $R^{12}$ is a tertiary carbon group, $R^{16}$, $R^{17}$ and $R^{21}$ may be hydrogen.

Preferably, when $R^{12}$ is a primary carbon group, zero to two of $R^{16}$, $R^{17}$ and $R^{21}$ is a primary carbon group and the remainder is hydrogen. When $R^{12}$ is a secondary carbon group, zero or one of $R^{16}$, $R^{17}$ and $R^{21}$ is a primary or secondary carbon group and the remainder is hydrogen. When $R^{12}$ is a tertiary carbon group, $R^{16}$, $R^{17}$ and $R^{21}$ are each hydrogen. Two adjacent groups of $R^{12}$ to $R^{21}$ may be bonded to each other to form a ring.

$M^2$, $X^1$, $Y^1$, m and n in Formula (7) are the same as defined in Formula (6). Preferred $M^2$ is iron, cobalt or nickel, and iron is particularly preferred. $X^1$ and $Y^1$ are preferably halogen (more preferably chlorine) or $C_{1-20}$ hydrocarbon group (more preferably methyl).

The following combination of the substituents is preferable in Formula (7).

$R^8$ and $R^9$ are each methyl or hydrogen; and/or $R^5$, $R^6$ and $R^7$ are all hydrogen; and/or $R^{13}$, $R^{14}$, $R^{15}$, $R^{17}$, $R^{18}$, $R^{19}$ and $R^{20}$ are all hydrogen; and/or $R^{12}$ and $R^{21}$ are each independently methyl, ethyl, propyl or isopropyl, preferably both are methyl or ethyl; and/or $X^1$ and $Y^1$ are each monovalent anion, preferably selected from halide and cyanide.

The following combinations of the substituents are also preferable. Namely, when $R^{12}$ is a primary carbon group, $R^{16}$ is a primary carbon group and $R^{17}$ and $R^{21}$ are each hydrogen. Alternatively, when $R^{12}$ is a secondary carbon group, $R^{16}$ is a primary or secondary carbon group, preferably a secondary carbon group and $R^{17}$ and $R^{21}$ are each hydrogen. When $R^{12}$ is a tertiary carbon group, $R^{16}$, $R^{17}$ and $R^{21}$ are each hydrogen.

The following combinations of $R^5$ to $R^9$ and $R^{12}$ to $R^{21}$ are particularly preferable for Formula (7):

(a) $R^8=R^9=$methyl, $R^5=R^6=R^7=R^{13}=R^{14}=R^{15}=R^{16}=R^{17}=R^{18}=R^{19}=R^{20}=$hydrogen, and $R^{12}=R^{21}=$methyl;

(b) $R^8=R^9=$methyl, $R^5=R^6=R^7=R^{13}=R^{14}=R^{15}=R^{16}=R^{17}=R^{18}=R^{19}=R^{20}=$hydrogen, and $R^{12}=R^{21}=$ethyl;

(c) $R^8=R^9$=methyl, $R^5=R^6=R^7=R^{13}=R^{14}=R^{15}=R^{16}=R^{17}=R^{18}=R^{19}=R^{20}$=hydrogen, and $R^{12}=R^{21}$=isopropyl;

(d) $R^8=R^9$=methyl, $R^5=R^6=R^7=R^{13}=R^{14}=R^{15}=R^{16}=R^{17}=R^{18}=R^{19}=R^{20}$=hydrogen, and $R^{12}=R^{21}$=n-propyl;

(e) $R^8=R^9$=methyl, $R^5=R^6=R^7=R^{13}=R^{15}=R^{16}=R^{17}=R^{18}=R^{20}$=hydrogen, and $R^{12}=R^{14}=R^{19}=R^{21}$=methyl;

(f) $R^8=R^9$=methyl, $R^5=R^6=R^7=R^{13}=R^{14}=R^{15}=R^{16}=R^{17}=R^{18}=R^{19}=R^{20}$=hydrogen, and $R^{12}=R^{21}$=chlorine; and (g) $R^8=R^9$=methyl, $R^5=R^6=R^7=R^{13}=R^{14}R^{15}R^{16}=R^{17}=R^{18}=R^{19}=R^{20}$=hydrogen, and $R^{12}=R^{21}$=trifluoromethyl.

In any of the above combinations, $X^1$ and $Y^1$ are each preferably halide or cyanide, and more preferably chlorine.

The transition metal compound represented by Formula (7) can be produced, for example, by reacting a ketone compound represented by the following Formula (8):

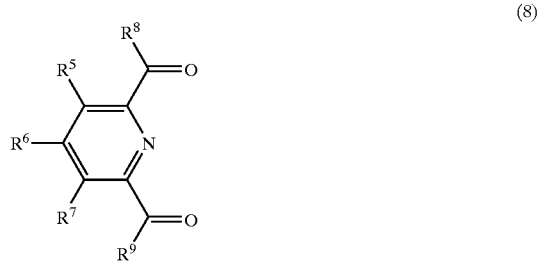

(8)

with an amine compound represented by $H_2NR^{22}$ or $H_2NR^{23}$ wherein $R^{22}$ and $R^{23}$ are

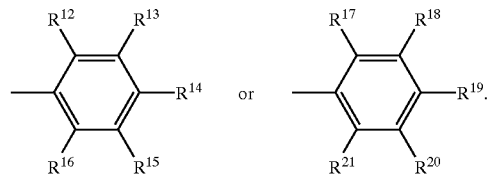

The reaction may be conducted in the presence of an organic acid such as formic acid as a catalyst. The compound obtained from the above reaction may be then reacted with a halide of transition metal $M^2$, for example a metal halide, to obtain the transition metal compound of Formula (7).

The component (A) is preferably a complex of Group 8 to 10 transition metal of the Periodic Table. Any of the transition metal complexes of Formulas (3) and (4) may be used as the complex of Group 8 to 10 transition metal of the Periodic Table, and preferred are nitrogen-containing iron chelate complexes, nitrogen-containing cobalt chelate complexes and nitrogen-containing nickel chelate complexes. Also, the transition metal complexes may be used alone or in combination of two or more.

Component (B)

The component (B) is a clay, clay mineral or ion-exchangeable layered compound. The clay is a substance composed of agglomerated fine hydrous silicate minerals, exhibits plasticity when kneaded with an appropriate amount of water and hardness when dried, and is sintered when burnt at high temperatures. The clay mineral is a hydrous silicate forming a substantial part of clay. Either of clay or clay mineral, which may be natural or synthetic, may be used for preparing the catalyst for polymerizing vinyl compounds.

The ion-exchangeable layered compound is preferably a compound having a layered, crystalline structure comprising stacked, parallel layers of atoms bonded to each other by ion bonding, etc. Respective layers are weakly bonded and ions therein are exchangeable. Some clay minerals are ion-exchangeable, layered compounds.

Example of the clay mineral as the component (B) include phyllosilicate minerals such as phyllosilicic acid and a phyllosilicate. Natural phyllosilicates include smectite group minerals such as montmorillonite, saponite and hectorite, mica group minerals such as illite and sericite, and mixed layered minerals of smectite group and mica group or mica group and vermiculite group. Synthesized phyllosilicates include Tetrasilicon Fluoride Mica, Laponite and Smecton. In addition, non-clay, ionic crystalline compounds having a layered crystalline structure such as $\alpha$-$Zr(HPO_4)_2$, $\gamma$-$Zr(HPO_4)_2$, $\alpha$-$Ti(HPO_4)_2$ and $\gamma$-$Ti(HPO_4)_2$ may be used.

Other usable clays and clay minerals not classified into the ion-exchangeable, layered compound include bentonite clay with a lower content of montmorillonite, Kibushi clay or gairome clay containing montmorillonite with other major components, fibrous sepiolite or palygorskite, and amorphous or low crystalline allophane or imogolite.

Of these substances as the component (B), preferred are silicon-containing layered compounds such as phyllosilicate minerals and mica group minerals. Preferred phyllosilicate minerals are smectite group minerals such as montmorillonite (also referred to as purified bentonite and coarse bentonite according to contents, etc.), saponite, etc. Preferred mica group minerals are Tetrasilicon Fluoride Mica known as synthesized mica, etc. Tetrasilicon Fluoride Mica is generally in the form of non-swelled or swelled micas, and preferred are swelled micas. In the present invention, the combination of iron chelate complex as the component (A) and smectite or mica as the component (B) is preferably used.

The component (B) is preferably in the form of particle having a volume average particle size of 3 $\mu$m or less. Particles generally have a specific size distribution. The particle of the component (B) preferably has a size distribution in which the volume average particle size is 10 $\mu$m or less and the content of particles having a volume average particle size of 3.0 $\mu$m or less is 10% by weight or more, more preferably a size distribution in which the volume average particle size is 10 $\mu$m or less and the content of particles having a volume average particle size of 1.5 $\mu$m or less is 10% by weight or more. The volume average particle size and the content of particles of a given volume average particle size may be determined by a laser transmission particle size analyzer such as CIS-1 manufactured by Galai Production Ltd.

The component (B) may be pretreated with acids, alkalis, salts or organic compounds. Of such pretreated component, those pretreated with quaternary ammonium salts, amine compounds, adducts of amine and Brønsted acid, or organosilane compounds are preferable in view of polymerization activity.

The quaternary ammonium salts may be quaternary alkylammonium salts, quaternary arylammonium salts, quaternary arylalkylammonium salts, quaternary benzylammonium salts and heteroaromatic ammonium salts, although not specifically limited thereto. Examples of the quaternary alkylammonium salts include tetra-n-propylammonium chloride, tetrabutylammonium chloride, dimethyldicyclohexylammonium chloride, methyltri-n-octylammonium chloride, methyltris(2-ethylhexyl)ammonium chloride, methyl-tri-n-decylammonium chloride, methyl-tri-n-octylammonium chloride, methyl-tri-n-dodecylammonium chloride and dimethyl-di-n-octadecylammonium dichloride.

Examples of the quaternary arylammonium salts include tetraphenylammonium chloride, etc. Examples of the quaternary arylalkylammonium salts include phenyltrimethylammonium chloride, dimethyldiphenylammonium chloride and methyltriphenylammonium chloride. Examples of the quaternary benzylammonium salts include dimethyldibenzylammonium chloride and methyltribenzylammonium chloride. Examples of the heteroaromatic ammonium salts include N-methyl-2-benzylpyridinium chloride, N-methyl-3-benzylpyridinium chloride, N-methyl-4-benzylpyridinium chloride, N-methyl-2-phenylpyridinium chloride, N-methyl-3-phenylpyridinium chloride and N-methyl-4-phenylpyridinium chloride. Bromides, fluorides and iodides corresponding to the above chlorides may be used as the quaternary ammonium salts. In the quaternary ammonium salt, the ratio of the number of carbon atoms to the number of nitrogen atoms is preferably 8 or more. More preferred are quaternary ammonium salts having at least one aromatic ring-containing group such as the quaternary benzylammonium salts, quaternary arylammonium salts and quaternary arylalkylammonium salts; and quaternary ammonium salts having two or more alkyl groups having 6 or more carbon atoms such as dimetyldicyclohexylammonium chloride, methyltri-n-octylammonium chloride, methyltris(2-ethylhexyl)ammonium chloride, methyltri-n-decylammonium chloride, methyltri-n-octylammonium chloride, methyltri-n-dodecylammonium chloride and dimetyldi-n-octadecylammonium chloride. The quaternary ammonium salt is used in an amount of 0.001 to 2 mmol, preferably 0.01 to 1 mmol per unit weight (g) of the component (B) such as clay, etc.

Examples of the amine compounds include primary amines such as stearylamine and octylamine; secondary amines such as N-stearyl-N-methylamine and N-octyl-N-methylamine; and tertiary amines such as tribenzylamine, N,N-dibenzyl-N-phenylamine and N,N-dimethyl-N-phenylamine. The amine compound may be used in the form of an adduct with Brønsted acid. Examples of the Brønsted acids include hydrochloric acid, sulfuric acid and phosphoric acid. The adduct of the amine compound and the Brønsted acid is used in an amount of 0.01 to 10 mmol, preferably 0.1 to 1 mmol per unit weight (g) of the component (B) such as clay, etc.

The organosilane compound is represented, although not particularly limited, by the following Formula (9):

$$R^{24}_p SiX^2_{4-p} \qquad (9)$$

wherein $R^{24}$ is hydrogen or a group having a carbon or silicon atom which is directly bonded to Si; $X^2$ is halogen or a group having an oxygen or nitrogen atom which is directly bonded to Si; p is an integer from 1 to 3, and a plurality of $R^{24}$ groups or $X^2$ groups, if any, may be the same or different from each other.

The organosilane compound of Formula (9) includes polynuclear polysiloxane, polysilazane and bis-silyl compound represented by Formula (10):

$$X^2_{4-p} Si(CH_2)_q SiX^2_{4-p} \qquad (10)$$

wherein q is an integer from 1 to 10; $X^2$ and p are the same as defined in Formula (9).

Examples of the organosilane compounds of Formula (9) include trialkylsilyl chlorides, dialkylsilyl dichlorides, diarylsilyl dichlorides and alkylarylsilyl dichloriodes such as trimethylsilyl chloride, triethylsilyl chloride, triisopropylsilyl chloride, t-butyldimethylsilyl chloride, t-butyldiphenylsilyl chloride, phenethyldimethylsilyl chloride, dimethylsilyl dichloride, diethylsilyl dichloride, diisopropylsilyl dichloride, di-n-hexylsilyl dichloride, dicyclohexylsilyl dichloride, docosylmethylsilyl dichloride, bis(phenethyl)silyl dichloride, methylphenethylsilyl dichloride, diphenylsilyl dichloride, dimesitylsilyl dichloride and ditolylsilyl dichloride.

Other examples of the organosilane compounds of Formula (9) include silyl halides obtained by substituting chlorine of the above compounds with another halogen; disilazanes such as bis(trimethylsilyl)amide, bis(triethylsilyl) amide, bis(triisopropylsilyl) amide, bis(dimethylethylsilyl) amide, bis(diethylmethylsilyl)amide, bis(dimethylphenylsilyl)amide, bis(dimethyltolylsilyl)amide and bis(dimethylmenthylsilyl)amide; trialkylsilyl hydroxides such as trimethylsilyl hydroxide, triethylsilyl hydroxide, triisopropylsilyl hydroxide, t-butyldimethylsilyl hydroxide and phenethyldimethylsilyl hydroxide; polysilanols known as a peralkylpolysiloxypolyol; bissilyl compounds such as bis(methyldichlorosilyl)methane, 1,2-bis(methyldichlorosilyl)ethane, bis(methyldichlorosilyl)octane and bis(triethoxysilyl)ethane; and hydride-containing silanes such as dimethylchlorosilane, (N,N-dimethylamino) dimethylsilane and diisobutylchlorosilane.

Examples of the organosilane compounds represented by Formula (10) include bissilyl compounds such as bis(methyldichlorosilyl)methane, 1,2-bis(methyldichlorosilyl)ethane, bis(methyldichlorosilyl)octane and bis(triethoxysilyl)ethane. The polynuclear polysiloxane may be cyclic polysiloxanes such as 1,3,5,7-tetramethylcyclotetrasiloxane, 1,3,5,7-tetraethylcyclotetrasiloxane and 1,3,5,7-tetramethyl-1,3,5,7-tetraphenylcyclotetrasiloxane; and linear polysiloxanes such as 1,1,5,5-tetraphenyl-1,3,3,5-tetramethyltrisiloxane. Examples of the polysilazane include disilazanes such as bis(trimethylsilyl) amide, bis(triethylsilyl) amide, bis(triisopropylsilyl) amide, bis(dimethylethylsilyl) amide, bis(diethylmethylsilyl) amide, bis(dimethylphenylsilyl)amide, bis(dimethyltolylsilyl)amide and bis(dimethylmenthylsilyl) amide.

The organosilane compounds may be used alone or in combination of two or more.

Of these organosilane compounds, preferred are those having at least one alkyl group ($R^{24}$) such as alkylsilyl halides, especially diaklylsilyl halides. The pretreatment of the component (B) with the organosilane compound is effectively conducted in the presence of water. In this case, water allows the coarse particles of clay, etc. to be finely dispersed, and changes the layered structure of clay, thereby enhancing the contact efficiency of the organosilane compound with clay, etc. Namely, water increases the distance between crystalline layers of clay, etc. to promote the reaction between the organosilane compound and clay, etc. The organosilane compound is used 0.001 to 1000 mol, preferably 0.01 to 100 mol in terms of silicon atom per one kilogram of the component (B).

The pretreatment of the component (B) may be performed, for example, by the following method. The clay, clay mineral or ion-exchangeable layered compound is dispersed in water to prepare an aqueous dispersion into which a quaternary ammonium salt, an amine salt or Brønsted acid adduct thereof, or an organosilane compound is then added, followed by heating the mixture. The resulting slurry (hydrophobicized product) was filtered, and the obtained filter cake is dried.

Preferably, the component (B) is pretreated with the quaternary ammonium salt. Preferred examples of the component (B) suitably pretreated with the quaternary ammonium salt are those having a high capability of adsorbing the quaternary ammonium salt, or those having a high capability of producing a layered compound (also referred to as an intercalation compound) by the reaction with clay, etc. For example, clays and clay minerals are preferable. More specifically, the component (B) is preferably phyllosilicate minerals, more preferably smectite, and most preferably montmorillonite. Tetrasilicon fluoride mica is preferable as the synthesized phyllosilicate.

Component (C)

The component (C) is an aluminoxy compound represented by the following Formula (1):

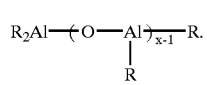

(1)

In the above Formula (1), a plurality of R groups are each independently $C_{1-10}$ hydrocarbon group, and at least one of the R groups is a hydrocarbon group having 2 or more carbon atoms. Apart of the R groups may be methyl, but a majority (at least one half) of the R groups are preferably hydrocarbon groups having 2 or more carbon atoms. Examples of $C_{1-10}$ hydrocarbon groups include straight-chain hydrocarbon groups such as methyl, ethyl, n-propyl and n-hexyl; and branched hydrocarbon groups such as isopropyl, isobutyl and t-butyl. Examples of the hydrocarbon groups having 2 or more carbon atoms include straight-chain hydrocarbon groups such as ethyl, n-propyl and n-hexyl; and branched hydrocarbon groups such as isopropyl, isobutyl and t-butyl. Preferred R is ethyl or isobutyl in view of higher activity of the obtained catalyst. The suffix x is an integer of 2 or more, usually 2 to 100, preferably 2 to 50, more preferably 2 to 10, and most preferably 2 to 4. When x is 2 to 4, the obtained catalyst exhibits a higher activity. Most preferred is an aluminoxy compound wherein R is ethyl or isobutyl and x is 2 to 4, and specifically a tetraethyl dialuminoxane, pentaethyl trialuminoxane and tetraisobutyl dialuminoxane.

The aluminoxy compounds are preferably soluble in saturated hydrocarbon solvents such as n-hexane, n-heptane and cyclohexane in view of good handling ability and higher catalytic activity.

The aluminoxy compound may be produced by reacting a trialkylaluminum compound with water, or by hydrolyzing a dialkylaluminum halide. The aluminoxy compound prepared by these methods sometimes contains an unreacted organoaluminum compound or a cyclic aluminoxy compound. In the present invention, although the component (C) is mainly the aluminoxy compound, those containing such an unreacted organoaluminum compound and cyclic aluminoxy compound may also be used as the component (C).

Of these aluminoxy compounds represented by the Formula (1), preferred are those produced by reacting the organoalumium compound with water.

Next, the process for producing the catalyst for polymerizing vinyl compounds according to the present invention is described. The catalyst for polymerizing vinyl compounds is prepared by contacting the components (A), (B) and (C) with each other. The components (A) and (B) may be first contacted with each other, and then the component (C) may be contacted with the components (A) and (B). The component (B) dehydrated in advance is preferably contacted with component (A) in view of improved activity of the obtained catalyst. The contact temperature is room temperature, preferably from room temperature to 100° C., and the contact time is 10 minutes or more, preferably 15 minutes or more, more preferably one hour or more. The contact is preferably conducted in the presence of a highly polar solvent. The higher the polarity of the solvent, the higher the efficiency of contact between the components, thereby shortening the contact time. Examples of the solvents include aromatic hydrocarbons such as toluene and xylene.

The amount of the transition metal complex used as the component (A) is 0.1 to 1000 μmol, preferably 1 to 100 μmol, and the amount of the component (C) is 0.01 to 20 mmol, preferably 0.1 to 10 mmol, each based on unit weight (g) of the component (B) such as clay, etc.

[II] Process for Production of Vinyl Polymers

In the process for the production of vinyl polymers according to the present invention, a vinyl compound is polymerized in the presence of the above catalyst optionally containing an organometallic compound (D). Examples of the organometallic compounds are organoaluminum compounds, organomagnesium compounds, organolithium compounds and organozinc compounds. In view of low costs and easy availability, preferred are the organoaluminum compounds exemplified by trialkylaluminums such as trimethylaluminum, triethylaluminum, tripropylaluminum, triisobutylaluminum and tri-t-butylaluminum; halogen- or alkoxy-containing alkylaluminums such as dimethylaluminum chloride, diethylaluminum chloride, dimethylaluminum methoxide and diethylaluminum ethoxide; and methylalumoxane. Of these organoaluminum compounds, preferred is the trialkylaluminum, and more preferred is triisobutylaluminum. The amount of the optional component (D) is 0.1 to 1000 mmol, preferably 0.5 to 50 mmol based on unit weight (g) of the component (B) such as clay, etc.

Examples of the vinyl compounds are olefins, styrene, styrene derivatives, acrylic derivatives and vinyl esters of fatty acids.

Olefins are not strictly limited, and preferably α-olefins having 2 to 20 carbon atoms. Examples of such α-olefins include ethylene, propylene, 1-butene, 1-pentene, 1-hexene, 1-heptene, 1-octene, 1-nonene, 1-decene, 4-phenyl-1-butene, 6-phenyl-1-hexene, 3-methyl-1-butene, 4-methyl-1-butene, 3-methyl-1-pentene, 4-methyl-1-hexene, 5-methyl-1-hexene, 3,3-dimethyl-1-pentene, 3,4-dimethyl-1-pentene, 4,4-dimethyl-1-pentene and vinylcyclohexane. Examples of the other olefins usable in the present invention include dienes such as 1,3-butadiene, 1,4-pentadiene and 1,5-hexadiene; halogenated α-olefins such as hexafluoropropene, tetrafluoroethylene, 2-fluoropropene, fluoroethylene, 1,1-difluoroethylene, 3-fluoropropene, trifluoroethylene and 3,4-dichloro-1-butene; and cyclic olefins such as cyclopenetene, cyclohexene, norbornene, 5-methylnorbornene, 5-ethylnorbornene, 5-propylnorbornene, 5,6-dimethylnorbornene and 5-benzylnorbornene. Examples of the styrene derivatives include alkylstyrenes such as p-methylstyrene, p-ethylstyrene, p-propylstyrene, p-isopropylstyrene, p-butylstyrene, p-t-butylstyrene, p-phenylstyrene, o-methylstyrene, o-ethylstyrene, o-propylstyrene, o-isopropylstyrene, m-methylstyrene, m-ethylstyrene, m-isopropylstyrene, m-butylstyrene, mesitylstyrene, 2,4-dimethylstyrene, 2,5-dimethylstyrene and 3,5-dimethylstyrene; alkoxystyrenes such as p-methoxystyrene, o-methoxystyrene and m-methoxystyrene; halogenated styrenes such as p-chlorostyrene, m-chlorostyrene, o-chlorostyrene, p-bromostyrene, m-bromostyrene, o-bromostyrene, p-fluorostyrene, m-fluorostyrene, o-fluorostyrene and o-methyl-p-fluorostyrene; trimethylsilylstyrene; vinyl benzoate; and divinylbenzene. Examples of the acrylic derivatives include ethyl acrylate, butyl acrylate, methyl methacrylate and ethyl methacrylate. Examples of the vinyl esters of fatty acids include vinyl acetate, isopropenyl acetate and vinyl acrylate.

In the process of the present invention, the vinyl compound may be used alone or in combination of two or more. When the copolymerization is intended, two or more of the above olefins may be combined arbitrarily.

In the process of the present invention, the above α-olefins having 2 to 20 carbon atoms may be copolymerized with another monomer exemplified by chain diolefins such as butadiene, isoprene, 1,4-pentadiene and 1,5-hexadiene; polycyclic olefins such as norbornene, 1,4,5,8-dimetano-1,2,3,4,4a,5,8,8a-octahydronaphthalene and 2-norbornene; cyclic diolefins such as norbornadiene, 5-ethylidenenorbornene, 5-vinylnorbornene and dicyclopentadiene; and unsaturated esters such as ethyl acrylate and methyl methacrylate.

The vinyl compound is preferably ethylene, propylene or styrene, and more preferably ethylene. The method for polymerizing vinyl compounds is not particularly limited and may be carried out by any known methods such as slurry polymerization, solution polymerization, vapor-phase polymerization, bulk polymerization and suspension polymerization, preferably by solution polymerization. In addition, the polymerization may be carried out in either continuous manner or batch-wise manner. As the solvent, if used, an aliphatic hydrocarbon solvent such as butane, pentane, hexane, heptane, each including all isomers, and cyclohexane may be used. Of the above solvents, cyclohexane is particularly preferable because the deterioration of the product purity due to formation of alkylated by-product can be effectively avoided as compared with using aromatic hydrocarbon solvent such as toluene. The solvent may be used singly or in combination of two or more. When the solvent is used, the amount of catalyst in terms of the component (A) contained therein is generally 0.01 to 100 μmol, preferably 0.1 to 20 μmol per one liter solvent in view of obtaining sufficient reactivity.

The polymerization conditions are not specifically limited. The reaction temperature is generally −78 to 200° C., preferably room temperature to 150° C. The reaction pressure is generally ordinary pressure to 15 MPa·G, preferably ordinary pressure to 5 MPa·G. The molecular weight can be controlled by know methods, for example, by suitably selecting the temperature and pressure. When the vinyl compounds are polymerized using the catalyst of the present invention, vinyl-terminated α-olefins (oligomer) having a number average molecular weight of 10,000 or less or polyolefins having a number average molecular weight of more than 10,000 can be efficiently produced with low costs.

[III] Catalyst for Production of α-Olefin Oligomers

The catalyst for producing α-olefins comprises (A') a complex of Group 8 to 10 transition metal of the Periodic Table, (B') an organic compound-modified, clay, clay mineral or ion-exchangeable layered compound, and (C') at least one aluminoxy compound represented by the following general Formula (2):

(2)

wherein a plurality of R groups are each independently $C_{1-10}$ hydrocarbon group, and at least one of the R groups is a hydrocarbon group having 2 or more carbon atoms; and y is an integer of 2 to 4.

When the complex of Group 8 to 10 transition metal of the Periodic Table is used in combination with the organic compound-modified, clay, clay mineral or ion-exchangeable layered compound, the respective catalyst components are rendered insoluble in a reaction solvent (hydrocarbon), so that the catalyst is readily separated from the reaction mixture after completion of the oligomerization reaction without deactivation thereof.

Component (A')

The complex of Group 8 to 10 transition metal of the Periodic Table is preferably selected from chelate complexes represented by the general Formulas (5) and (6). More preferred are chelate complexes represented by the general Formulas (5) and (6) in which $M^2$ is iron, cobalt or nickel; and $X^1$ and $Y^1$ are each halogen, especially chlorine, or $C_{1-20}$ hydrocarbon group, especially methyl. Example of the preferred $R^1$ to $R^4$ groups and the preferred $R^5$ to $R^{11}$ groups are the same as described above.

Component (B')

The component (B') is prepared by modifying clay, clay mineral or ion-exchangeable layered compound selected from those exemplified as the component (B), with an organic compound. Examples of the organic compounds used for the modification of the component (B) include quaternary ammonium salts, amine compounds, adducts of amine and Brønsted acid or organosilane compounds. Of these organic compounds, the quaternary ammonium salts and the organosilane compounds are preferred.

The clay, clay mineral or ion-exchangeable layered compound may be modified with the organic compound in the following manner. The clay, clay mineral or ion-exchangeable layered compound is dispersed in water to prepare an aqueous dispersion, into which the quaternary ammonium salt, the amine salt, the adduct of amine and Brønsted acid or the organosilane compound is then added, followed by heating the mixture. The resulting slurry (hydrophobicized product) was filtered, and the obtained filter cake is dried.

For the modification of the clay, clay mineral or ion-exchangeable layered compound, the quaternary ammonium salt is used in an amount of 0.01 to 10 mmol, preferably 0.1 to 1 mmol; the amine salt or the adduct of amine and Brønsted acid is used in an amount of 0.01 to 10 mmol, preferably 0.1 to 1 mmol; and the organosilane compound is used in an amount of 0.1 to 100 mmol, preferably 0.5 to 10 mmol, each based on one gram of the clay, etc.

Component (C')

The component (C') is the aluminoxy compound represented by the following general Formula (2):

(2)

In Formula (2), R is the same as defined in Formula (1); and y is an integer of 2 to 4. A part of a plurality of R groups may be methyl, but a majority (at least one half) of the R groups are preferably hydrocarbon groups having 2 or more carbon atoms.

The catalyst for producing α-olefins according to the present invention may be prepared by preliminarily contacting the components (A') and (B') and then contacting the component (C') in a reaction system for oligomerization of ethylene, or by preliminarily contacting the components (B') and (C') and then contacting the component (A') with the components (B') and (C'). For example, the components to be contacted are dispersed in an aromatic hydrocarbon solvent such as toluene and xylene, and the resulting mixture is stirred at room temperature, preferably at a temperature of from room temperature to 100° C., for 10 minutes or more, preferably 15 minutes or more, and more preferably one hour or more.

In any of the above preparation methods, when the clay, clay mineral or ion-exchangeable layered compound modified with the organic compound is used, the components (A') and (C') are adsorbed into layers of the component (B'), so that the respective catalyst components are rendered insoluble in a reaction solvent (hydrocarbon) for the oligomerization. On the contrary, the use of a large amount of the conventional methylaluminoxane results in not only deteriorated catalytic activity but also failure to keep the excess amount of methylaluminoxane in a solid state during the reaction. As a result, a large amount of the methylaluminoxiane is transferred into liquid phase in the subsequent solid-liquid separation step, thereby causing problems such as deposition of metal component (aluminum compound) within a distiller. In order to prevent the catalyst components from being eluted into liquid phase and improve the activity of the catalyst, it is essential to use the aluminoxy compound represented by Formula (2).

The component (C') is used in an amount of 0.01 to 10 mmol, preferably 0.1 to 5 mmol in terms of aluminum atom per unit weight (g) of the component (B'). The component (A') is used in an amount of 0.5 to 100 $\mu$mol, preferably 1 to 20 $\mu$mol in terms of transition metal per unit weight (g) of the component (B'). When the amount of the component (A') exceeds the above range, the component (B') fails to adsorb the whole amount of the component (A'), thereby causing the elution of the component (A') into liquid phase in the solid-liquid separation step. With such a formulation, the catalyst for the production of $\alpha$-olefins according to the present invention is still kept in a solid state even after completion of the oligomerization without the elution of the catalyst components into liquid phase. As a result, the catalyst is readily separated from the reaction solution by solid-liquid separation, thereby smoothly performing the subsequent purification of $\alpha$-olefins by distillation.

[IV] Process for Producing $\alpha$-Olefins

In the process of the present invention, $\alpha$-olefins (oligomers) may be produced by oligomerizing ethylene in the presence of the catalyst containing the above components (A'), (B') and (C') and optionally the organometallic compound (D).

The optional organometallic compound (D) is used in an amount of 0.1 to 1,000 mmol, preferably 0.5 to 50 mmol based on unit weight (g) of the component (B').

The oligomerization of the $\alpha$-olefin monomers may be carried out by any known methods such as slurry polymerization, solution polymerization, vapor-phase polymerization, bulk polymerization and suspension polymerization, preferably by solution polymerization. In addition, the oligomerization may be carried out in either continuous manner or batch-wise manner. As the solvent for the oligomerization, an aliphatic hydrocarbon solvent such as butane, pentane, hexane, heptane, each including all isomers, and cyclohexane may be used. When the solvent is used, the amount of the catalyst in terms of the component (A') is generally 0.01 to 100 $\mu$mol, preferably 0.1 to 20 $\mu$mol per one liter solvent.

The oligomerization conditions are not specifically limited. The reaction temperature is generally 0 to 150° C., preferably room temperature to 150° C. The reaction pressure is generally ordinary pressure to 15 MPa·G, preferably ordinary pressure to 5 MPa·G. The oligomer distribution during the oligomerization can be controlled by any know methods, for example, by suitably selecting the temperature and pressure. The oligomers are produced according to Schulz-Flory distribution rule. The oligomer distribution depends on K-value which changes from 0.4 to 0.8. When the K-value is 0.4, the content of 1-butene becomes higher, and when the K-value is 0.8, the content of high-molecular weight wax becomes higher. In the present invention, the K value is preferably 0.5 to 0.7.

After completion of the oligomerization, the reaction mixture is subjected to solid-liquid separation. The solid-liquid separation may be practically and simply carried out by centrifugally separating the reaction mixture into a solid phase (catalyst and by-produced polymer) and a liquid phase ($\alpha$-olefins and oligomerization solvent). The centrifugal force and the centrifugal separation time required for the solid-liquid separation varies depending upon kind and particle size of the component (B'), and usually 10 to 10,000 G and 1 second to 10 minutes, respectively. For example, when montmorillonite having an average particle size of 0.1 $\mu$m is used as the component (B'), the solid-liquid separation of the reaction mixture is sufficiently accomplished by the centrifugal separation at a centrifugal force of 125 G for one minute.

When the solid-liquid separation is carried out at 100° C. or higher, the by-produced polymer is dissolved in the reaction solvent, resulting in undesirable precipitation of the by-produced polymer in the subsequent solvent removal and oligomer purification by distillation. Accordingly, the solid-liquid separation is preferably carried out at 0 to 90° C., more preferably 20 to 80° C.

In the process of the present invention for producing $\alpha$-olefins, vinyl-terminated $\alpha$-olefins (oligomers) having a number average molecular weight of 10,000 or less are efficiently produced with low costs.

The present invention will be described in more detail with reference to the following examples. However, it should be noted that the following examples are only illustrative and not intended to restrict the scope of the present invention thereto.

EXAMPLE 1

(1) Preparation of Clay-Quaternary Ammonium Salt Slurry A

Into a 2-liter flask containing one liter of distilled water, 2.5 g of Na-montmorillonite (BEN-GEL, available from Hojun Yoko, Co., Ltd.) were slowly added under stirring. Thereafter, stirring was continued for two hours at room temperature to prepare a clay-water colloidal solution. After heating the clay-water colloidal solution to 60° C., an aqueous solution prepared by dissolving 0.792 g (2 mmol) of benzylcetyldimethyl ammonium chloride in 100 ml of water was added thereto. After the addition, the mixture was stirred for one hour at the same temperature. The resultant slurry was filtered under heating through a pressure filter. The separated solid product was vacuum-dried at room temperature to obtain 3.1 g of clay-quaternary ammonium salt composite.

A 300-ml Schlenk tube was charged with 1.0 g of the clay-quaternary ammonium salt composite and 200 ml of toluene. After heating to 100° C., the mixture was stirred for one hour at the same temperature and cooled to obtain a clay slurry. The supernatant of the clay slurry was discarded by a cannula, and the volume of the slurry was adjusted to 50 ml by adding toluene to obtain the clay-quaternary ammonium salt composite slurry A (clay-quaternary ammonium salt composite content: 20 mg/ml).

(2) Preparation of Catalyst Slurry A

Into 20 ml of toluene, was suspended 0.088 g (200 μmol) of a pyridinebisimine iron complex, [2,6-[(2,4-$C_6H_3Me_2$)N=C(Me)]$_2C_5H_3N$]FeCl$_2$, which was prepared according to the method described in J. Am. Chem. Soc., 1998, 4049 and Chem. Commun., 1998, 849, thereby preparing a complex slurry A (complex content: 10 μmol/ml). In a Schlenk tube, 5.0 ml of the clay-quaternary ammonium salt composite slurry A and 0.2 ml of the complex slurry A were mixed and stirred for two hours at room temperature to prepare a catalyst slurry A.

(3) Oligomerization

Into a 1.6-liter autoclave of 50° C., 400 ml of dry cyclohexane, 0.13 ml of a toluene solution (Al content: 1.0 mol/liter) of tetraisobutyldialuminoxane, [($CH_3$)$_2CHCH_2$]$_2$AlOAl[$CH_2CH(CH_3)_2$]$_2$ (compound represented by Formula (1) in which all R groups are isobutyl and x is 2, or by Formula (2) in which all R groups are isobutyl and y is 2), and all of the catalyst slurry A prepared above were successively added in nitrogen stream (molar ratio between metals: Al/Fe=65). Thereafter, ethylene was pumped into the autoclave to keep the reaction pressure at 0.8 MPa·G. Thirty minutes after starting the introduction of ethylene, the supply of ethylene was stopped and the reaction liquid was rapidly cooled by cooling water. After cooling and pressure release, 138.4 g (total yield) of the reaction product containing 0.82 g of solid cyclohexane insolubles, i.e., polymer and 137.5 g of cyclohexane solubles were obtained. The total polymerization activity and the polymerization activity for the cyclohexane solubles were 2476 kg/gFe/h and 2462 kg/gFe/h, respectively. $^{13}$C-NMR measurement showed that the polymer obtained was a vinyl-terminated polymer. Gas chromatographic analysis showed that 99% by weight of the cyclohexane solubles was a vinyl-terminated, linear (α-olefin (hereinafter occasionally referred to merely as "oligomer"). In the gas chromatographic analysis, OV-1 column (60 m) was used for determining the amount of oligomer and Ultra-2 column (50 m) was used for determining the purity.

EXAMPLE 2

The oligomerization of ethylene was conducted in the same manner as in Example 1(3) except for changing the amount of the toluene solution of tetraisobutyldialuminoxane, [($CH_3$)$_2CHCH_2$]$_2$AlOAl[$CH_2CH(CH_3)_2$]$_2$, (Al content: 1.0 mol/liter) from 0.13 ml to 0.25 ml.

As a result, 73.2 g (total yield) of the reaction product containing 0.59 g of solid cyclohexane insolubles, i.e., polymer and 72.61 g of cyclohexane solubles were obtained. The total polymerization activity and the polymerization activity for the cyclohexane solubles were 1311 kg/gFe/h and 1300 kg/gFe/h, respectively. $^{13}$C-NMR measurement showed that the polymer obtained was a vinyl-terminated polymer. Further, the same Gas chromatographic analysis as in Example 1 showed that 99% by weight of the cyclohexane solubles was a vinyl-terminated, linear α-olefin.

EXAMPLE 3

The oligomerization of ethylene was conducted in the same manner as in Example 1(3) except for changing the amount of the toluene solution of tetraisobutyldialuminoxane, [($CH_3$)$_2CHCH_2$]$_2$AlOAl[$CH_2CH(CH_3)_2$]$_2$, (Al content: 1.0 mol/liter) from 0.13 ml to 0.50 ml.

As a result, 40.0 g (total yield) of the reaction product containing 0.46 g of solid cyclohexane insolubles, i.e., polymer and 39.54 g of cyclohexane solubles was obtained. The total polymerization activity and the polymerization activity for the cyclohexane solubles were 716 kg/gFe/h and 708 kg/gFe/h, respectively. $^{13}$C-NMR measurement showed that the polymer obtained was a vinyl-terminated polymer. Further, the same Gas chromatographic analysis as in Example 1 showed that 98% by weight of the cyclohexane solubles was a vinyl-terminated, linear α-olefin.

EXAMPLE 4

(1) Preparation of Clay-Quaternary Ammonium Salt Slurry B

Into a 300-ml Schlenk tube, were added 1.0 g of S-BEN 78 (organic bentonite available from Hojun Yoko Co., Ltd.; montmorillonite containing a quaternary ammonium salt having long-chain ($C_{16-18}$) alkyl group) and 200 ml of toluene to prepare a clay dispersion. After heating to 100° C., the resultant dispersion was stirred for one hour at the same temperature and allowed to cool to obtain a clay slurry. The supernatant of the clay slurry was discarded by a cannula, and the volume of the slurry was adjusted to 50 ml by adding toluene to obtain the clay-quaternary ammonium salt composite slurry B (clay-quaternary ammonium salt composite content: 20 mg/ml).

(2) Preparation of Catalyst Slurry B

The catalyst slurry B was prepared in the same manner as in Example 1(2) except for using 5 ml of the clay-quaternary ammonium salt composite slurry B and 0.2 ml of the complex slurry A.

(3) Oligomerization

The oligomerization of ethylene was conducted in the same manner as in Example 3(2) except for using the catalyst slurry B instead of the catalyst slurry A. As a result, 31.9 g (total yield) of the reaction product containing 0.32 g of solid cyclohexane insolubles, i.e., polymer and 31.58 g of cyclohexane solubles was obtained. The total polymerization activity and the polymerization activity for the cyclohexane solubles were 571 kg/gFe/h and 565 kg/gFe/h, respectively. $^{13}$C-NMR measurement showed that the polymer obtained was a vinyl-terminated polymer. Further, the same Gas chromatographic analysis as in Example 1 showed that 97% by weight of the cyclohexane solubles was a vinyl-terminated, linear α-olefin.

EXAMPLE 5

The oligomerization of ethylene was conducted in the same manner as in Example 3(2) except for using a pentaisobutyltrialuminoxane, [($CH_3$)$_2CHCH_2$]$_2$AlOAl[$CH_2CH(CH_3)_2$]OAl[$CH_2CH(CH_3)_2$]$_2$, (compound represented by Formula (1) in which all R groups are isobutyl and x is 3, or by Formula (2) in which all R groups are isobutyl and y is 3) instead of the tetraisobutyldialuminoxane, [($CH_3$)$_2CHCH_2$]$_2$AlOAl[$CH_2CH(CH_3)_2$]$_2$. As a result, 28.1 g (total yield) of the reaction product containing 0.32 g of solid cyclohexane insolubles, i.e., polymer and 27.78 g of cyclohexane solubles were obtained. The total polymerization activity and the polymerization activity for the cyclohexane solubles were 503 kg/gFe/h and 497 kg/gFe/h, respectively. $^{13}$C-NMR measurement showed that the polymer obtained was a vinyl-terminated polymer. Further, the same Gas chromatographic analysis as in Example 1 showed that 97% by weight of the cyclohexane solubles was a vinyl-terminated, linear α-olefin.

Comparative Example 1

The oligomerization of ethylene was conducted in the same manner as in Example 1(3) except for using 0.13 ml of a toluene solution (Al content: 1.0 mol/liter) of methylalumoxane (available from Albemarle Corp.; a mixture of $(CH_3)_2Al[OAl(CH_3)]_{n-1}CH_3$ wherein n is 2 to 40 and n is 8 in average) instead of 0.13 ml of the toluene solution (Al content: 1.0 mol/liter) of tetraisobutyldialuminoxane, $[(CH_3)_2CHCH_2]_2AlOAl[CH_2CH(CH_3)_2]_2$. As a result, 4.8 g (total yield) of the reaction product containing 0.47 g of solid cyclohexane insolubles, i.e., polymer and 4.33 g of cyclohexane solubles were obtained. The total polymerization activity and the polymerization activity for the cyclohexane solubles were 347 kg/gFe/h and 314 kg/gFe/h, respectively. $^{13}$C-NMR measurement showed that the obtained polymer contained no terminal vinyl. Further, the same Gas chromatographic analysis as in Example 1 showed that 94% by weight of the cyclohexane solubles was a vinyl-terminated, linear α-olefin.

Comparative Example 2

The oligomerization of ethylene was conducted in the same manner as in Example 3(2) except for using triisobutyl aluminum, $[(CH_3)_2CHCH_2]_3Al$, corresponding to a compound represented by Formula (1) in which all R groups are isobutyl and x is 1, or by Formula (2) in which all R groups are isobutyl and y is 1, instead of the tetraisobutyldialuminoxane, $[(CH_3)_2CHCH_2]_2AlOAl[CH_2CH(CH_3)_2]_2$. As a result, 14.5 g (total yield) of the reaction product containing 0.27 g of solid cyclohexane insolubles, i.e., polymer and 14.23 g of cyclohexane solubles were obtained. The total polymerization activity and the polymerization activity for the cyclohexane solubles were 259 kg/gFe/h and 255 kg/gFe/h, respectively. $^{13}$C-NMR measurement showed that the obtained polymer contained no terminal vinyl. Further, the same Gas chromatographic analysis as in Example 1 showed that 97% by weight of the cyclohexane solubles was a vinyl-terminated, linear α-olefin.

EXAMPLE 6

Two 150-ml columns were respectively filled with 100 ml of the reaction solution obtained in Example 1, and set in a centrifugal separator SCR18B manufactured by Hitachi Kosoku Reikyaku Enshinki Co., Ltd. The separator was then operated at 5000 rpm (centrifugal force: 3160 G) for one minute to centrifugally separate the reaction solution. As a result, the reaction solution was completely separated into a liquid phase and a solid phase to give a transparent supernatant and a pasty semisolid. The supernatant was measured to determine the amounts of iron, aluminum, nitrogen and polymer contained therein. Specifically, the iron content was determined by analyzing a solution prepared by heat-treating the concentrated supernatant with hydrochloric acid using an inductively coupled plasma atomic emission spectrometer (ICP-AES). The aluminum content was determined by dissolving the concentrated supernatant in a mixed acid of concentrated sulfuric acid and hydrofluoric acid and subjecting the resultant solution to ICP-AES measurement. The nitrogen content was determined by measuring the supernatant by a total nitrogen analyzer. The content of the by-produced polymer dissolved in cyclohexane was expressed by the amount of the residues which were obtained by concentrating the supernatant in a weighing bottle at room temperature, and vacuum-drying the concentrate at 150° C. for one hour.

As a result of the above measurements, it was confirmed that the supernatant contained iron in an amount less than the lower detectable limit (less than 0.1 ppm), 7 ppm of aluminum, nitrogen in an amount less than the lower detectable limit (less than 1 ppm) and 250 ppm of the by-produced polymer.

EXAMPLE 7

Two 150-ml columns were respectively filled with 100 ml of the reaction solution obtained in Example 1, and set in a centrifugal separator. The separator was operated at 1000 rpm (125 G) for one minute to centrifugally separate the reaction solution. As a result, the reaction solution was completely separated into a liquid phase and a solid phase to give a transparent supernatant and a pasty semisolid. The supernatant was examined in the same manner as in Example 6. The results showed that the supernatant contained iron in an amount less than the lower detectable limit, 8 ppm of aluminum, nitrogen in an amount less than the lower detectable limit and 250 ppm of the by-produced polymer.

EXAMPLE 8

Two 150-ml columns were respectively filled with 100 ml of the reaction solution obtained in Example 1, and set in a centrifugal separator. The separator was then operated at 570 rpm (30 G) for 3 minutes to centrifugally separate the reaction solution. As a result, the reaction solution was completely separated into a liquid phase and a solid phase to give a transparent supernatant and a pasty semisolid. The supernatant was examined in the same manner as in Example 6. The results showed that the supernatant contained iron in an amount less than the lower detectable limit, 12 ppm of aluminum, nitrogen in an amount less than the lower detectable limit and 330 ppm of the by-produced polymer.

Reference Example

The reaction solution obtained in Example 1 was stirred again, and allowed to stand for one minute to sample 300 ml of suspended supernatant. The thus sampled supernatant was concentrated and extracted with ethanol. The extract was subjected to ICP-AES analysis to determine the amount of iron and aluminum contained therein. An ethanol extract obtained in the same manner as above was analyzed by a total nitrogen analyzer to determine the amount of nitrogen contained therein. The content of the by-produced polymer was calculated by subtracting the weight of residues (clay) after baking the concentrated supernatant from the weight of dried product (polymer and clay) obtained by vacuum-drying the concentrated supernatant.

The results showed that the supernatant contained 11 ppm iron, 1240 ppm of aluminum, 8 ppm of nitrogen and 4500 ppm of the by-produced polymer.

INDUSTRIAL APPLICABILITY

Vinyl-terminated, linear α-olefins (oligomers) having a number average molecular weight of 10,000 or less or polyolefins having a number average molecular weight of larger than 10,000 can be efficiently produced with low costs by using the catalyst of the present invention. The oligomers can be used as comonomers for olefin polymerization for producing LLDPE, etc. or materials for synthetic lubricant oils and cleaning agents.

In the catalyst for producing α-olefins according to the present invention, the catalyst components necessary for the oligomerization of ethylene are adsorbed between layers of the clay, clay mineral or ion-exchangeable layered compound modified with the organic compound. Therefore, the catalyst is kept in a solid state even after the oligomerization, thereby facilitating the separation of the catalyst from the reaction mixture. Further, since the separation of the catalyst is accomplished without deactivation, the ligand of the transition metal complex is prevented from being dissociated from the center metal, thereby producing high-boiling ethylene oligomers at a high purity. In addition, the use of a specific aluminoxy compound in the catalyst prevents aluminum compounds from dissolving into liquid phase and inhibits metal components from depositing within a distiller, resulting in facilitated operation of the apparatus.

What is claimed is:

1. A catalyst comprising
   (A') a diimine-containing complex compounds represented by the following Formula (5)

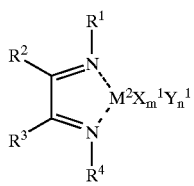

(5)

wherein $M^2$ is a Group 8 to 10 transition metal of the Periodic Table; $R^1$ and $R^4$ are each independently $C_{1-20}$ aliphatic hydrocarbon group, phenyl or $C_{7-20}$ aromatic group having a hydrocarbon group on its aromatic ring; $R^2$ and $R^3$ are each independently hydrogen or $C_{1-20}$ hydrocarbon group, and may be bonded together to form a ring; $X^1$ and $Y^1$ may be the same or different and are each a covalent- or ion-bonding group, and a plurality of $X^1$ groups and a plurality of $Y^1$ groups may be respectively the same or different; and m and n are each 0 or a positive integer, and the sum of m and n is 0, 1, 2 or 3 depending on the valence of $M^{2,}$ or a complex represented by the general Formula (6):

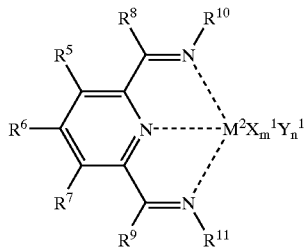

(6)

wherein $M^2$ is a Group 8 to 10 transition metal of the Periodic Table; $R^5$ to $R^9$ are each independently hydrogen, halogen, hydrocarbon group, substituted hydrocarbon group or heteroatom-containing hydrocarbon group, and may be bonded to each other to form a ring when each represents the hydrocarbon group; $R^{10}$ and $R^{11}$ are each independently $C_{1-160}$ aliphatic hydrocarbon group or $C_{7-160}$ aromatic group having a hydrocarbon group on the aromatic ring; $X^1$ and $Y^1$ may be the same or different and are each a covalent- or ion-bonding group, and a plurality of $X^1$ groups and a plurality of $Y^1$ groups may be respectively the same or different from each other; and m and n are each 0 or a positive integer and the sum of m and n is 0, 1, 2 or 3 depending on the valence of $M^{2,}$ (B') a clay, clay mineral or ion-exchangeable layered compound, modified with at least one organic compound selected from the group consisting of quaternary ammonium salts, amine compounds, and adducts of amine and Brönsted acid, and (C') at least one aluminoxy compound represented by the general Formula (2):

(2)

wherein a plurality of R groups are each independently $C_{1-10}$ hydrocarbon group and at least one of the R groups is a hydrocarbon group having 2 or more carbon atoms; and y is an integer of 2 to 4.

2. The catalyst according to claim 1, wherein the component (A') is a complex of a transition metal selected from the group consisting of nickel, cobalt and iron.

3. The catalyst according to claim 1, wherein the component (B') is a silicon-containing ion-exchangeable layered compound modified with an organic compound.

4. The catalyst according to claim 1, wherein the organic compound used for modifying the clay, clay mineral or ion-exchangeable layered compound is quaternary ammonium salts.

5. The catalyst according to claim 1, wherein the component (A') is an iron complex, and the component (B') is an organic compound-modified smectite or mica.

6. The catalyst according to claim 1, wherein R of the component (C') is ethyl or isobutyl.

7. A process for producing α-olefins, comprising a step of oligomerizing ethylene in the presence of the catalyst as defined in claim 1.

8. The process according to claim 7, wherein the oligomerization is performed in a saturated hydrocarbon as a polymerization solvent.

9. The process according to claim 7, wherein residue of the catalyst and by-produced polymer are separated from a reaction product by solid-liquid separation method.

10. The process according to claim 9, wherein the solid-liquid separation method is a centrifugal separation method.

11. The process according to claim 10, wherein the centrifugal separation method is performed at a temperature of 100° C. or lower.

12. A catalyst comprising
    (A) a diimine-containing complex compounds represented by the following Formula (5):

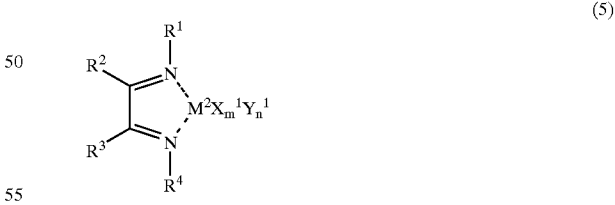

(5)

wherein $M^2$ a Group 8 to 10 transition metal of the Periodic Table; $R^1$ and $R^4$ are each independently $C_{1-20}$ aliphatic hydrocarbon group, phenyl or $C_{7-20}$ aromatic group having a hydrocarbon group on its aromatic ring; $R^2$ and $R^3$ are each independently hydrogen or $C_{1-20}$ hydrocarbon group, and may be bonded together to form a ring; $X^1$ and $Y^1$ may be the same or different and are each a covalent- or ion-bonding group, and a plurality of $X^1$ groups and a plurality of $Y^1$ groups may be respectively the same or different; and m and n are each 0 or a positive integer, and the sum of m and n is 0, 1, 2 or 3 depending on the valence of $M^2$, (B) a clay, clay mineral or ion-exchangeable layered compound pretreated with at least an organic compound selected from the group consisting of quaternary ammonium salts, amine compounds, and adducts of amine and Brönsted acid, and (C) at least one aluminoxy compound represented by the general Formula (1):

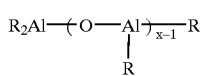 (1)

wherein a plurality of R groups are each independently $C_{1-10}$ hydrocarbon group and at least one of the R groups is a hydrocarbon group having 2 or more carbon atoms; and x is an integer of 2 or more.

13. The catalyst according to claim 12, wherein the component (A) is a complex of a transition metal selected from the group consisting of nickel, cobalt, and iron.

14. The catalyst according to claim 12, wherein the component (B) is a silicon-containing, ion-exchangeable layered compound modified with an organic compound.

15. The catalyst according to claim 12, wherein the component (A) is an iron complex, and the component (B) is an organic compound-modified smectite or mica.

16. The catalyst according to claim 12, wherein R of the component (C) is ethyl or isobutyl.

17. The catalyst according to claim 13, wherein R of the component (C) is ethyl or isobutyl.

18. The catalyst according to claim 14, wherein R of the component (C) is ethyl or isobutyl.

19. A process for producing vinyl polymers, comprising a step of polymerizing at least one vinyl compound selected from the group consisting of olefins, styrene, styrene derivatives, acrylic acid derivatives and vinyl esters of fatty acids, in the presence of the catalyst as defined in claim 12.

20. The process according to claim 17, wherein the vinyl compound is ethylene, propylene or styrene.

21. The process according to claim 17, wherein the polymerization of said vinyl compound is conducted in a saturated hydrocarbon compound as a polymerization solvent.

22. The process according to claim 17, wherein the vinyl polymers are vinyl-terminated oligomers having a number average molecular weight of 10,000 or less.

23. A catalyst comprising (A) a complex represented by the general Formula (6):

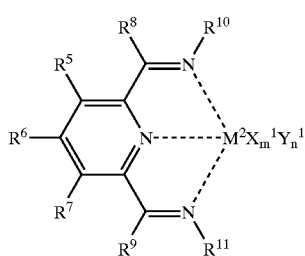 (6)

wherein $M^2$ is a Group 8 to 10 transition metal of the Periodic Table; $R^5$ to $R^9$ are each independently hydrogen, halogen, hydrocarbon group, substituted hydrocarbon group or heteroatom-containing hydrocarbon group, and may be bonded to each other to form a ring when each represents the hydrocarbon group; $R^{10}$ and $R^{11}$ are each independently $C_{1-160}$ aliphatic hydrocarbon group or $C_{7-160}$ aromatic group having a hydrocarbon group on the aromatic ring; $X^1$ and $Y^1$ may be the same or different and are each a covalent- or ion-bonding group, and a plurality of $X^1$ groups and a plurality of $Y^1$ groups may be respectively the same or different from each other; and m and n are each 0 or a positive integer and the sum of m and n is 0, 1, 2 or 3 depending on the valence of $M^2$.

(B) a clay, clay mineral or ion-exchangeable layered compound modified with at least one organic compound selected from the group consisting of quaternary ammonium salts, amine compounds, and adducts of amine and Brönsted acid, and (C) at least one aluminoxy compound represented by the general Formula (1):

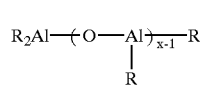 (1)

wherein a plurality of R groups are each independently $C_{1-10}$ hydrocarbon group and at least one of the R groups is a hydrocarbon group having 2 or more carbon atoms; and x is an integer of 2 or more.

24. The catalyst according to claim 23, wherein the component (A) is a complex of a transition metal selected from the group consisting of nickel, cobalt, and iron.

25. The catalyst according to claim 23, wherein the component (B) is a silicon-containing, ion-exchangeable layered compound.

26. The catalyst according to claim 23, wherein the component (A) is an iron complex, and the component (B) is smectite or mica.

27. The catalyst according to claim 23, wherein R of the component (C) is ethyl or isobutyl.

28. The catalyst according to claim 24, wherein R of the component (C) is ethyl or isobutyl.

29. The catalyst according to claim 25, wherein R of the component (C) is ethyl or isobutyl.

30. The catalyst according to claim 26, wherein R of the component (C) is ethyl or isobutyl.

31. A process for producing vinyl polymers, comprising a step of polymerizing at least one vinyl compound selected from the group consisting of olefins, styrene, styrene derivatives, acrylic acid derivatives and vinyl esters of fatty acids, in the presence of the catalyst as defined in claim 23.

32. The process according to claim 31, wherein the vinyl compound is ethylene, propylene or styrene.

33. The process according to claim 31, wherein the polymerization of said vinyl compound is conducted in a saturated hydrocarbon compound as a polymerization solvent.

34. The process according to claim 31, wherein the vinyl polymers are vinyl-terminated oligomers having a number average molecular weight of 10,000 or less.

* * * * *